United States Patent [19]
Bihari et al.

[11] Patent Number: 5,356,900
[45] Date of Patent: Oct. 18, 1994

[54] METHOD OF TREATING CHRONIC HERPES VIRUS INFECTIONS USING AN OPIATE RECEPTOR ANTAGONIST

[75] Inventors: Bernard Bihari, 29 W. 15th St., New York, N.Y. 10011; Finvola Drury, Rochester, N.Y.

[73] Assignee: Bernard Bihari, New York, N.Y.

[21] Appl. No.: 58,685

[22] Filed: May 10, 1993

Related U.S. Application Data

[63] Continuation of Ser. No. 973,545, Nov. 9, 1992, abandoned, which is a continuation of Ser. No. 839,277, Feb. 25, 1992, abandoned, which is a continuation of Ser. No. 658,662, Feb. 21, 1991, abandoned, which is a continuation of Ser. No. 433,152, Nov. 8, 1989, Pat. No. 5,013,739, which is a continuation-in-part of Ser. No. 129,862, Dec. 4, 1987, Pat. No. 4,888,346, which is a continuation of Ser. No. 916,180, Oct. 7, 1986, abandoned.

[51] Int. Cl.$^5$ ............................................. A61K 31/44
[52] U.S. Cl. ................................... 514/282; 514/934
[58] Field of Search ............................ 514/282, 934

[56] References Cited

U.S. PATENT DOCUMENTS

| | | | |
|---|---|---|---|
| 4,537,878 | 8/1985 | Plotnikoff | 514/2 |
| 4,927,832 | 5/1990 | Clemence et al. | 514/299 |
| 4,956,355 | 9/1990 | Prendergast | 514/178 |

*Primary Examiner*—Gary E. Hollinden
*Attorney, Agent, or Firm*—William J. Daniel

[57] ABSTRACT

Chronic herpes virus infections are treated in human patients by the administration by a pharmacologically effective mode or route of an essentially pure opiate receptor antagonist, preferably an essentially pure opiate receptor antagonist exhibiting substantially higher blocking action against Mu opiate receptor sites than against Delta receptor sites, exemplified by Naltrexone and Naloxone, at a low dose concentration which produces therapeutic results corresponding to those produced by Naltrexone when administered in the range of 1 mg to 10 mg and at which Delta receptor blocking activity is at most small while Mu receptor blocking activity is significant and most preferably exclusive.

6 Claims, No Drawings

5,356,900

METHOD OF TREATING CHRONIC HERPES VIRUS INFECTIONS USING AN OPIATE RECEPTOR ANTAGONIST

CROSS REFERENCE TO RELATED APPLICATION

This application is a continuation of application Ser. No. 07/973,545 filed Nov. 9, 1992 abandoned which is a continuation of 07/839,277, filed Feb. 25, 1992, now abandoned which is a continuation of 07/658,662, filed Feb. 21, 1991, now abandoned which is a continuation of 07/433,152, filed Nov. 8, 1989, now U.S. Pat. No. 5,013,739, which is a continuation-in-part of 07/129,862, filed Dec. 4, 1987, now U.S. Pat. No. 4,888,346 which is a continuation of 06/916,180, fled Oct. 7, 1986, now abandoned.

FIELD OF THE INVENTION

This invention relates to the treatment of certain chronic diseases; namely, chronic infections caused by herpes virus, both herpes simplex virus and Epstein-Bart virus, and multiple sclerosis, by the low dose administration of an essentially pure opiate receptor antagonist, such as naltrexone and naloxone.

BACKGROUND OF THE INVENTION

In our application Ser. No 129 862 and its parent, identified above, we disclosed and claimed the treatment of humans infected with HTLV-III (AIDS) virus, including clinically diagnosed AIDS and AIDS-related complex (ARC), by the administration at low dosage levels of an essentially pure opiate receptor antagonist, preferably such antagonist having preferential blocking activity for Mu over Delta opiate receptor sites and exhibiting at the contemplated low dosage level a substantially selective blocking activity for Mu over Delta receptor sites, exemplified by naltrexone and naloxone. The patent literature relating to the medical utility proposed at the time for these and related drugs is summarized in the introductory discussion of the earlier application, the complete contents of which are hereby incorporated by reference, and include the treatment of narcotic addiction and narcotic overdose, the relief of severe itching in conjunction with Hodgkins Disease, mycosis funoides, severe jaundice, and various types of pruritis, the treatment of anorexia, the treatment of medical shock; i.e., anaphylactic, burn, cardiac, and the like shock, and the treatment of alcoholism or alcoholic intoxication.

As explained in the prior applications, essentially pure opiate receptor antagonists, exemplified by naltrexone and naloxone, appear to be effective in potentiating the natural human immune system against the HTLV-III (AIDS) virus, apparently by up-regulation of the endorphinergic system to thereby enhance homostatic regulation of the natural immune function of the human body in ways by no means adequately understood. It has now been discovered that surprisingly these drugs are likewise effective for the treatment of certain chronic long-term diseases for which a specific medical treatment has been largely unavailable up to now, and even their etiology is, in a majority of instances, unknown.

DETAILED DESCRIPTION OF THE INVENTION

The diseases with which the invention is particularly concerned are listed below, together with a summary description of their pertinent medical features,

Chronic Herpes Virus Infections

The important herpes virus infections are chronic genital herpes and chronic infections due to the Epstein-Barr virus (EPV). Genital herpes is a highly prevalent disease caused by the herpes simplex virus (HSV) type No. 2, transmitted from person to person by direct contact. The disease typically begins with a genital rash and mild itching which develops into vesicular lesions appearing mainly on the getitalia and adjacent body regions, which lesions can expand to an ulcerated condition, which can be accompanied by a general malaise, fever and anorexia. Neurological complications are possible but rare. The disease is often self-limiting and may disappear after a single episode or, more typically, can reoccur in milder and less frequent episodes; but for some, it can be become chronic with severe and painful episodes at weekly or monthly intervals. Such episodes can be precipitated by stress, trauma, menstrual hormone changes, etc. The chronic disease is usually associated with high levels of serum antibodies against HSV. There is presently no cure for genital herpes. Treatment with the anti-viral drug, acylovir, administered in topical form appears to limit episodic duration but does not effect a cure, prevent transmission or protect against subsequent reoccurance. Otherwise, treatment is generally palliative. Substantial risk exists for infants delivered by normal birth from infected mothers; neonatal herpes can cause brain damage and possible death.

EBV is the cause of infectious mononucleosis which occurs mainly in late adolescence and young adults by transmission of the virus through direct oral contact. Its symptoms are "flu-like" and mainly include headache, sore throat, muscle soreness, swollen glands, and general fatigue and weakness. These symptoms usually dissipate within a few weeks and treatment consists mainly of rest and curtailed activities combined with analgesic administration to relieve pain and soreness, there being no curative treatment known. Occasionally, the condition becomes recurrent or chronic which is particularly indicated by serological evidence of EBV and a significant increase in lymphocytes, with a large atypical fraction, In chronic cases, the "flu-like" symptoms may persist for a considerable period, and it is this category with which the invention is concerned.

Multiple Sclerosis

MS is a chronic neurological disease resulting in destruction of the myelin covering of nerve cells, particularly of the brain and spinal cord. It affects men and women equally, mainly between the ages of 20 and 40. Etiological evidence is mixed. Certain evidence suggests an infectious (vital) factor since occurrence is far more common in temperate regions than in tropical regions. Other evidence suggests autoimmune involvement changes in the seriology of the autoimmune system being usually evident prior to acute attacks. Still further evidence suggests a genetic predisposition, persons of Oriental and African ancestry being generally free of the disease independently of origin of birth. Or a combination of all three could be involved in that exposure to a virus at an early age, by which most individuals are unaffected, could after a period of latency trigger in genetically susceptible individuals an autoimmune response. Symptoms of the disease include physical weakness, loss of muscular coordination, unusual burning or prickling sensation and disturbances of speech and vision, especially double vision. Diagnosis is difficult and usually requires a considerable history. For some, the disease may effectively disappear after an attack or two with no disabling consequences. More generally, there is a pattern of relapse and spontaneous remission over time with progressive neurologic disfunction, causing increasing spasticity and loss of coordination. There is no curative treatment for MS; severity of a relapse may be reduced by treatment with corticosteroids, but without apparent long term beneficial effect. Administration of immuno-suppressive agents and interferon have proved ineffective. Treatment is by rest and exercise and aims mainly at diminishing the severity of the physical effects of the disease and adaptive adjustment of the patient's lifestyle.

Our copending application Ser. No. 07/433,152 identified above is directed to the treatment of chronic fatigue syndrome in the same manner as here. In early studies of chronic fatigue syndrome, an association was found with high levels of antibodies against EBV, but later evidence has questioned the validity of this association, at least in terms of a casual relationship, the EBV antibody level:variations frequently lacking a statistical significance or even being within normal limits in some cases.

Recent press reports indicate that the antiviral agent acyclovir, otherwise effective against EPV, was no more effective than a placebo in treating CFS, thus putting into question the etiological involvement of EBV in this malady.

The distinction between CFS, chronic EBV infection and/or chronic infectious mononucleosis is presently unclear.

The above disease summaries were extracted in simplified and condensed form from *The Encyclopedia and Dictionary of Medicine, Nursing, and Allied Health* by Miller and Keane, W. B. Saunders Co. 3rd Edition, April 1983, and Cecil *Essentials of Medicine* by Andreolin et al, W. B. Saunders Co., copyright 1986.

In view of the highly diverse nature of the several diseases with which this invention is concerned, it is quite unexpected that they could be successfully treated by the administration of the essentially pure opiate antagonists of the invention, especially at the extremely low dosage levels herein contemplated. MS has an apparent association with autoimmune action but for such action, enhancement of the natural immune function of the body, as is believed to be achieved by the invention, would seem to be directly contraindicated. Indeed, as the above discussions indicate, treatment with immunosuppressive agents has been considered as one approach in the management of this disease. As regards herpes infections, to the extent that a chronic state of infection might indicate an impairment of the immune function of the body, it is nonetheless surprising that the treatment of the invention could induce such a significant improvement in immune function as to actually prove efficacious for these diseases.

The therapeutic agents useful in the present method are the essentially pure opiate antagonists. It is generally accepted that drugs exert their characteristic physiological action in the body by inter:acting or complexing with certain so-called receptor sites existing in cells in the brain and elsewhere. An opiate antagonist has the capability of interacting with those specific receptor sites which are sensitive to opiate or narcotic drugs, and so long as such interaction persists and of thereby blocking such receptor sites from any additional interaction with the opiate drugs and in this manner preventing the opiate drugs from exerting their characteristic analgesic and euphoric action on the body. These opiate antagonists which do not exert any physiological action of their own are deemed essentially pure and are suitable for purposes of this invention, The great majority of drugs found to possess antagonist action also exert a significant agonist action and are referred to as "mixed agonist/antagonists". Such mixed agonist/antagonists are not suitable for use in the present method which requires essential purity in the antagonist effect.

There appear to be several different kinds of receptor sites that are sensitive to Opiates or narcotics, perhaps five or so, and the important sensitivity is possessed by those identified as Mu and Delta receptor sites. The Mu receptor sines have particularly strong affinity for opiate drugs and produce a correspondingly strong physiological (agonist) reaction upon interaction with such drugs. Blockage of the Mu receptor sites is hence an important objective of the invention. Any essentially pure opiate antagonist is effective in blocking Mu receptor sites and thus would be advantageous to at least some extent for achieving the therapeutic results of this invention.

Delta receptor sites, on the other hand, appear to contribute to an effectively functioning immune system when unblocked. It is, therefore, preferred to select an essentially pure opiate antagonist which possesses a preferential blocking action for Mu receptor sites over Delta receptor sites in order to leave the latter in unblocked condition. Such preferential blocking action of Mu sites over Delta sites may be dosage related; that is, a particular antagonist can have an effectively stronger blocking action for Mu sites than for Delta sites at a given dosage range; whereas at higher levels, the amount may be enough to block both sites in substantial entirety. By appropriate selection of the dosage level, one can achieve with a given antagonist, a significant and valuable blocking action against Mu receptor sites while maintaining the blocking action against Delta sites at appreciably lower levels at which the blocking effect on the Delta sites is minor or at least inconsequential. If increasingly higher dosages were to be employed, then ultimately both Mu and Delta sites would both become blocked, which is less advantageous in therapeutic results and preferably to be avoided. However, by judicious adjustment of the dosage level, one can take advantage of the differential between the Mu blocking and Delta blocking capabilities and achieve an effective blocking of Mu sites with only minimal blocking of the Delta sites which is optimum for therapeutic purposes.

Naltrexone and naloxone are both essentially pure opiate antagonists which also exert strong preferential blocking action against Mu over Delta sites, the Mu blocking action being generally rated at about ten times the Delta blocking action. Both of these drugs are presently commercially available and are, so far as is known, the only essentially pure opiate antagonists which have received governmental approval for administration to humans. Both of these drugs can be employed in the practice of this invention with naltrexone being the preferred choice. If other essentially pure opiate antagonists, preferably those exerting significant preferential action against Mu over Delta receptors, become available and receive governmental approval, such drugs, at least in principle, qualify for application in the present method.

The therapeutic agent should obviously be administered by a pharmacological mode or route of administration which is effective for the particular drug. Naltrexone can be administered effectively orally; i.e., in the form of tablets, capsules, caplets, powder, a powdered suspension or solution in a suitable liquid carrier or the like. It is not available in a form suitable for administration by injection. On the other hand, naloxone has not proved to be effective when administered orally at least at dosage levels which would be practical and appropriate in this invention. It is, however, available in forms-suitable for administration by injection and can be applied by this mode in the invention if desired. Generally, oral administration is preferable from the standpoint of simplicity and convenience and naltrexone is thus the preferred choice, However, for those patients for whom oral administration is not permissible, administration of naloxone by injection, either intravenously, intramuscularly, or subcutaneously, is an alternative.

The useful dosage range, at which Mu receptor sites are substantially blocked while the Delta sites are substantially unblocked, for naltrexone is about 1-10 mg/day daily. The limits of this range are not critical but below about 1 mg the therapeutic effect is quite small, while at levels several times above 10 mg, at which these drugs have been generally administered in the past for other purposes, especially narcotic addiction, the effects of the preferential blocking action against Mu over Delta receptor sites disappears, since the amount of the drug is large enough to cause at least substantial blocking of Delta sites while the Mu sites remain fully blocked. A preferred range for naltrexone is about 1.5-3.0 rag/day daily.

The dosage levels for naloxone and any other essentially pure opiate antagonist that might become available in the future are to be determined with reference to the above-specified dosage ranges for naltrexone. That is, the dosage level for naltrexone or any new essentially pure opiate antagonist should be such as to produce an antagonist effect which corresponds or is equivalent to that produced by naltrexone at the range of about 1-10 mg/day. Such equivalent amounts can be readily determined for other opiate antagonists. Morphine is well recognized as a classical Mu agonist, and other antagonists than naltrexone can be readily standardized against morphine to quantify the amounts thereof that are equivalent to the effective dosage for naltrexone. For example, by means of tests evaluating the response of rats or mice, e.g., the "tail flick" test, that amount of morphine which is offset or counteracted in its narcotic dependency effect by a given amount of naltrexone can then be nested against other antagonists to determine the specific amount of the latter which is necessary to produce the equivalent antagonist action against morphine as the naltrexone. For further information concerning such tests, reference may be had, for example, to the text *Principles of Drug Action: The Basis of Pharmacology*, Goldstein et al, second edition, copyright 1974, John Wiley & Sons, at pages 604-609 in particular.

EXAMPLES

1) Genital Herpes

A 50 year old woman has had genital herpes for 13 years, experiencing a severe painful attack with several lesions for the 4-5 days preceding each menstrual period during most of that time. She was started on low dose naltrexone (1.75 mg per day at bedtime). Her attacks immediately stopped. Ten months later the dosage was increased to 2.75 rag/day also taken at bedtime. In the entire period of naltrexone treatment covering a number of months, she has had only two attacks each occurring 2-3 weeks after she ran out of naltrexone and interrupted the treatment temporarily.

2) Multiple Sclerosis (M.S.)

A. A 26 year old woman had an attack of transverse myelitis several years ago at the lower thoracic level, with a paraparesis involving marked weakness and numbness of both legs. This gradually cleared over a two month period. Four months after the first attack, she had a second episode of transverse myelitis at the cervical level, with symptoms involving her arms and legs, and the diagnosis of multiple sclerosis was made. This gradually cleared. An attack of transverse myelitis at the lower thoracic level occurred four months later, her third attack in eight months. As she was recovering from this attack, she started on naltrexone, 1.75 mg per day at bedtime. Her only subsequent attack in the intervening period of many months occurred one year later, three weeks after she voluntarily discontinued naltrexone. This attack involved weakness and numbness of the left arm. She immediately resumed her low dose naltrexone treatment and has had no attacks since.

B. A 65 year old woman with M.S. of thirty years duration was started on naltrexone. Her M.S. is of the slow deteriorating type with slowly increasing weakness, spasticity and incoordination of her arms and legs with some deterioration apparent to her physicians-on each six months follow-up visit. Over a number of months since starting the naltrexone, the disease has stabilized and the progressive deterioration has stopped.

What is claimed is:

1. The method of treating humans suffering from chronic herpes virus infections, which comprises the step of administering by a pharmacologically effective mode to such patient an essentially pure opiate receptor antagonist having a selectively higher blocking action against Mu opiate receptors than against Delta receptors in an amount which is effective to exert a substantial opiate receptor blocking action against Mu receptors but insufficient to exert such action against Delta receptors.

2. The method of claim 1, wherein said opiate receptor antagonist is either naltrexone or naloxone.

3. A method of treating a human patient suffering from a chronic herpes infection which comprises the step of administering by a pharmacologically effective mode to such patient a therapeutically effective dose consisting essentially of an essentially pure opiate receptor antagonist, the amount of said dose being selected to produce therapeutic results substantially corresponding to those produced by Naltrexone when administered in the range of about 1 mg to about 10 mg.

4. The method of claim 3, wherein said disease is genital herpes.

5. A method of treating a human patient suffering from a chronic herpes infection which comprises the step of administering by a pharmacologically effective mode to such patient a therapeutical effective dose consisting essentially of an essentially pure opiate receptor antagonist, the amount of said dose being selected to produce therapeutic results corresponding substantially to those produced by Naltrexone when administered in the range of about 1 mg to about 10 mg and at a level within said range exerting an opiate blocking action substantially exclusively for Mu opiate receptors.

6. The method of claim 5, wherein said opiate receptor antagonist is either naltrexone or naloxone.

* * * * *